(12) United States Patent
Piene et al.

(10) Patent No.: US 7,638,143 B2
(45) Date of Patent: Dec. 29, 2009

(54) PROCESS FOR PREPARING ORAL CALCIUM COMPOSITIONS

(75) Inventors: Jan Yngvar Piene, Asker (NO); Dina Dogger Schmidt, Oslo (NO)

(73) Assignee: Nycomed Pharma AS (NO)

( * ) Notice: Subject to any disclaimer, the term of this patent is extended or adjusted under 35 U.S.C. 154(b) by 0 days.

(21) Appl. No.: 11/798,519

(22) Filed: May 15, 2007

(65) Prior Publication Data

US 2007/0224268 A1 Sep. 27, 2007

Related U.S. Application Data

(63) Continuation of application No. 10/973,352, filed on Oct. 27, 2004, now abandoned, which is a continuation of application No. 09/831,553, filed on Nov. 5, 2001, now abandoned, which is a continuation-in-part of application No. PCT/GB99/03666, filed on Nov. 5, 1999.

(30) Foreign Application Priority Data

Nov. 13, 1998 (GB) ................................. 9825033.5

(51) Int. Cl.
*A61K 33/06* (2006.01)
*A61K 33/10* (2006.01)
*A61K 33/42* (2006.01)

(52) U.S. Cl. .................. 424/687; 424/602; 424/682
(58) Field of Classification Search ...................... None
See application file for complete search history.

(56) References Cited

U.S. PATENT DOCUMENTS

| | | | | |
|---|---|---|---|---|
| 4,684,534 A | * | 8/1987 | Valentine | 424/441 |
| 4,814,177 A | * | 3/1989 | Walsdorf et al. | 424/464 |
| 5,437,873 A | * | 8/1995 | Phadke et al. | 424/465 |
| 5,506,211 A | * | 4/1996 | Barnes et al. | 514/27 |
| 5,629,013 A | * | 5/1997 | Upson et al. | 424/441 |
| 5,935,996 A | * | 8/1999 | Yamaguchi | 514/460 |
| 6,066,342 A | * | 5/2000 | Gurol et al. | 424/687 |
| 6,114,289 A | * | 9/2000 | Capeci et al. | 510/108 |
| 6,296,868 B1 | * | 10/2001 | Valentine et al. | 424/441 |
| 6,368,638 B1 | * | 4/2002 | Tiongson | 424/687 |
| 6,716,454 B2 | * | 4/2004 | Meignant et al. | 424/465 |

FOREIGN PATENT DOCUMENTS

| | | | |
|---|---|---|---|
| DE | 19617487 | | 11/1997 |
| EP | 192 460 | * | 8/1986 |
| EP | 0192460 | * | 8/1986 |
| EP | 0487774 | | 6/1992 |
| EP | 0931549 | | 7/1999 |
| FR | 2724844 | | 3/1996 |
| JP | 5-32554 | | 2/1993 |
| WO | WO96/09036 | * | 3/1996 |

OTHER PUBLICATIONS

Shire Pharmaceuticals Ltd., "Chemist & Druggist", Information Access Co., Apr. 4, 1992, ISSN: 0009-3033, p. 510.
Shire Pharmaceuticals Ltd., "Monthly Index of Medical Specialists", Nov. 1992.
Shire Pharmaceuticals Ltd., "Nutrition", British Pharmaceutical Product Catalogue MIMS, Feb. 1993, pp. 185.
P.J. Meunier, "Biochemical Response to Combined Vitamin D3 and Calcium Supplementation in Elderly People with Vitamin D Insufficiency", Ninth Workshop on Vitamin D, Marriott's Orlando World Center, Orlando, FL, May 28-Jun. 2, 1994.

* cited by examiner

*Primary Examiner*—Shaojia Anna Jiang
*Assistant Examiner*—Eric S Olson
(74) *Attorney, Agent, or Firm*—Bacon & Thomas, PLLC

(57) ABSTRACT

A process for the preparation of an orally administrable calcium composition comprising the steps of: (i) obtaining a physiologically tolerable particulate calcium compound having a mean particle size in the range 3 to 40 μm, having a crystalline structure and having a surface area of 0.1 to 1.2 $m^2/g$; (ii) mixing the calcium compound with a water-soluble diluent and an aqueous solution of a water soluble binder in a fluid bed granulation apparatus and drying the resulting mixture to produce a first granulate; (iii) optionally mixing the first granulate with one or more further components to produce a second granulate; and (iv) optionally compressing the first or second granulate to form tablets.

16 Claims, No Drawings

PROCESS FOR PREPARING ORAL CALCIUM COMPOSITIONS

This application is a continuation application of U.S. application Ser. No. 10/973,352, filed Oct. 27, 2004 (of which the entire disclosure of the parent application is hereby incorporated by reference), now abandoned, which is a continuation application of abandoned U.S. application Ser. No. 09/831,553, filed Nov. 5, 2001, (of which the entire disclosure of the prior application is hereby incorporated by reference) which is a continuation-in-part of PCT/GB99/03666, filed Nov. 5, 1999.

This invention relates to a process for the manufacture of an orally administrable pharmaceutical composition containing a physiologically tolerable calcium compound, in particular a composition in tablet form.

Calcium carbonate tablets are used as a source of calcium, especially for patients suffering from or at risk of osteoporosis. Moreover calcium carbonate is used as an acid neutralizing agent in antacid tablets.

Calcium carbonate is used in such tablets since the calcium content of calcium carbonate is high, the calcium is presented in a form which can be taken up from the gastrointestinal tract, calcium carbonate is effective at neutralizing gastric acids, and calcium carbonate is a physiologically acceptable calcium compound.

In such tablets, various binders, sweeteners and flavors are used in order to produce a tablet which is readily acceptable to the patient. Indeed many producers have sought to achieve improved patient acceptability by formulating the tablets with such excipients in a "chewable" form. As a result, and since the daily recommended dosage is generally about 1000 mg calcium, the commercially available calcium tablets which commonly contain 500 mg calcium are relatively bulky.

Examples of chewable calcium carbonate tablets are described in WO 96/09036 (Laboratoire Innothera) and in U.S. Pat. No. 4,446,135 (Sterling Drug). The chewable calcium carbonate tablets described in these two patent publications have a calcium carbonate content of about 50% or less by weight and for a 500 mg calcium dosage are therefore undesirably large.

The present invention is directed to a process by which this undesired bulk may be reduced, and in particular to a process by which a chewable calcium tablet may be produced with a calcium compound content in excess of 60% by weight.

Thus viewed from one aspect the present invention provides a process for the preparation of an orally administrable calcium composition, said process comprising the steps of:

(i) obtaining a physiologically tolerable particulate calcium compound having a mean particle size in the range 3 to 40 μm, having a crystalline structure and having a specific surface area of 0.1 to 1.2 m$^2$/g, preferably 0.2 to 0.9 m$^2$/g, especially 0.3 to 0.8 m$^2$/g;

(ii) mixing said calcium compound with a water-soluble diluent and an aqueous solution of a water soluble binder in a fluid bed granulation apparatus and drying the resulting mixture to produce a first granulate;

(iii) optionally mixing said first granulate with one or more further components to produce a second granulate, preferably a granulate having a content of said calcium compound of at least 60% by weight; and (iv) optionally compressing said first or second granulate to form tablets.

The physical characteristics of the calcium compound used in the process of the invention are important in order that the fluid bed granulation stage should produce a first granulate having the desired characteristics. The calcium compound should be crystalline and have a mean particle size of 3 to 40 μm, preferably 5 to 3 μm. Preferably it should have a bulk density in the range of 0.2 to 1.5 g/mL, more preferably 0.3 to 1.4 g/mL, especially 0.4 to 1.3 g/mL. The calcium compound is preferably an acid soluble compound, e.g. a compound poorly soluble or insoluble in water at pH7 but soluble in water at gastric pH values.

The upper particle size limit of 40 μm is important in order to avoid a gritty mouthfeel in the final product. The lower particle size limit of 3 μm is also important in order to avoid a feeling of stickiness on the teeth during chewing.

Crystallinity, in particular the possession of relatively smooth crystal surfaces and low specific surface area, is important for the achievement of effective and rapid wetting and granulation in the fluid granulation step of the process of the invention.

Specific surface area may be determined using apparatus such as the Carlo Erba Sorptomatic 1900.

The calcium compound may, for example, be selected from calcium carbonate, calcium lactate, calcium gluconate, calcium citrate, calcium glycerophosphate, calcium phosphate, calcium hydrogen phosphate (e.g. in tribasic, dibasic or monobasic forms, i.e. $Ca_3(PO_4)_2$, $CaHPO_4.2H_2O$ and $Ca(HPO_4)_2.H_2O$), calcium glucuronate, calcium aspartate, calcium glucoheptonate and mixtures of two or more thereof. However, calcium carbonate, in particular in calcite form, is preferred due to its high calcium content, its ready availability, its cost, its well-documented absorption characteristics in humans, and its performance in the fluid granulation step of the process of the invention.

Especially, preferably calcium carbonate having individual or primary and cubic or pseudo-cubic shaped calcite crystals with smooth or even surfaces are used. Desirably such crystals are also transparent. Where the end product is for use as a medicine, it is also preferred that the calcium carbonate be a material precipitated according to Ph. Eur.

Examples of appropriate commercially available calcium carbonate include Merck 2064 (available from Merck, Darmstadt, Germany), Scoralite 1A and Scoralite 1B (available from Scora Watrigant SA, France), Super-Purity $CaCO_3$ and Medicinal Heavy $CaCO_3$ (available from Shanghai Da Yu Biochemistry Co. Ltd., China), and Pharmacarb LL (available from Crompton & Knowles, Vineland, USA). Scoralite 1B and Scoralite 1A+1B are particularly preferred. Merck 2064 has a mean particle size of 10 to 30 μm, an apparent bulk density of 0.4 to 0.7 g/mL, and a specific surface area of 0.3 m$^2$/g; Scoralite 1A has a mean particle size of 5 to 20 μm, an apparent bulk density of 0.7 to 1.0 g/mL and a specific surface area of 0.6 m$^2$/g; Scoralite 1A+1B has a mean particle size of 7 to 25 μm, an apparent bulk density of 0.7 to 1.2 g/mL and a specific surface area of 0.35 to 0.8 m$^2$/g; Scoralite 1B has a mean particle size of 10 to 30 μm, an apparent bulk density of 0.9 to 1.3 g/mL and a specific surface area of 0.4 to 0.6 m$^2$/g; Medicinal Heavy $CaCO_3$ has a mean particle size of 5 to 30 μm, an apparent bulk density of 0.9 to 1.3 g/mL and a specific surface area of 0.8 m$^2$/g; Super-Purity $CaCO_3$ has a mean particle size of 10 to 30 μm, an apparent bulk density of 0.9 to 1.2 g/mL and a specific surface area of 0.6 m$^2$/g; and Pharmacarb LL has a mean particle size of 5 to 30 μm, an apparent bulk density of 0.8 to 1.2 g/mL and a specific surface area of 0.7 m$^2$/g. The Pharmacarb LL calcium carbonate however is not apparently a material precipitated in accordance with Ph. Eur. and thus is more preferred for production of end products which are for use as dietary supplements or food products than those which are for use as pharmaceuticals.

The calcium compound or mixture of calcium compound preferably makes up 60 to 95% by weight of the second granulate, and preferably provides a calcium content of 15 to 40%, more preferably 20 to 35%, and still more especially 25 to 30% by weight in the second granulate.

The calcium compound or mixture of compounds preferably makes up 60.5 to 96%, more preferably 66 to 91% still more preferably 68 to 80% and most preferably 72 to 76% by weight of the first granulate.

The water-soluble diluent used in step (ii) of the process of the invention is preferably a sweetener or a mixture of sweeteners, e.g. a polyol or a polysaccharide, more preferably a non-cariogenic sweetener. Examples of suitable diluents include sorbitol, xylitol, isomalt and mannitol, which are non-cariogenic. Neosorb P100T sorbitol, xylitol CM50 and isomalt PF are available commercially from Roquette Freres, Xyrofin and Palatinit respectively. Further examples of suitable saccharide-based diluents include sucrose, fructose and the maltodextrins (e.g. Lycatab DSH available from Roquette Freres). Especially preferred as diluents are the non-cariogenic oligosaccharides such as inulin and oligofructose. Inulin may be obtained by extraction from chickory root and is available under the trade name Raftiline from Orafti SA, Tieren, Belgium. Oligofructose is obtained by partial hydrolysis of inulin and is available from Orafti SA under the trade name Raftilose and from Beghin-Meiji Industries, Neuilly-sur-Seine, France under the trade name Actilight.

The diluent preferably makes up the major proportion, e.g. by 70 to 96%, more preferably 80 to 95%, still more preferably 85 to 94%, most preferably 90 to 92% of the total weight of diluent and binder in the first granulate.

The calcium compound and diluent (which, especially in the case of inulin, may be the same material as is used as the binder) are preferably blended before addition of the aqueous binder. The blending may conveniently be performed as a dry blending, for example using a blender with a rotating mixer arm, e.g. a blade. This ensures that any lumps are removed and achieves an intimate mixing of the calcium compound and the diluent. By way of example, a high speed mixer (e.g. Fielder PMA 25/2G) may be used operating at maximum speed for both the impeller and knife for two minutes; however any mill may be used to break up lumps in the mixture and indeed the calcium compound and the diluent may be treated in this way separately to remove lumps before they are blended.

The water-soluble binder used in step (ii) of the process of the invention may be selected from known water-soluble pharmaceutical binders, e.g. it may be a soluble cellulose or polysaccharide or a polyvinylpyrrolidone or a mixture thereof. Preferably the binder is a polyvinylpyrrolidone, e.g. Kollidon K30, Kollidon 90F or Kollidon VA64 which are available commercially from BASF. Inulin and maltodextrin may also be used as binders.

The binder is preferably used in aqueous solution at a concentration of 10 to 35% by weight, more especially 15 to 35%, preferably 25 to 30%, and particularly 27 to 29% by weight.

The fluid granulation step, step (ii) of the process of the invention, may be effected in any fluid granulation apparatus, e.g. a Glatt GPCG 3 fluid bed available from Glatt GmbH. The procedure preferably involves spraying the aqueous binder mixture onto the fluidized diluent/calcium compound mixture. Fluidization may be achieved by gas flow through the mixture or alternatively mechanically, e.g. by the use of counter-rotating, interlocking paddles with horizontal rotational axes. The liquid sprayed is preferably at or near ambient temperature (e.g. 15 to 35° C., preferably 20 to 30° C., more preferably about 25° C.) and the particulate onto which it is sprayed is again preferably at or near ambient temperature (e.g. 15 to 35° C., preferably 20 to 30° C., more preferably about 25° C.). The gas pressure of the spray chamber is conveniently ambient (e.g. 1 atmosphere). The spray rate may be adjusted, according to batch size and component identities and concentrations, to optimize the mean particle size of the first granulate. However, for a 3 kg solids batch, a spray rate of 30 to 50 g/min may be appropriate and a spray rate of about 40 g/min is particularly preferred.

The granulate may be dried in a separate drier but preferably is dried in place in the fluidized bed mixer, e.g. using a heated gas (e.g. air) flow through the granulate. This can be effected while spraying of the binder solution is taking place or after spraying of the binder solution has been completed. Clearly if drying is effected during spraying it should be completed after spraying has stopped. Preferably a drying gas temperature of 60 to 90° C., more especially 65 to 75° C., in particular about 70° C. is used. Particularly preferably drying is effected such that the granulate temperature reaches 40 to 50° C., especially about 43 to 45° C.

In this way a first granulate having a low water content, e.g. 1 to 5% by weight, preferably about 3%, may be produced and subsequently dried to a moisture content of about 0.1 to 0.5%, preferably 0.2% by weight, within an overall granulation and drying period of 15 to 45 mins, preferably 20 to 30 mins.

The first granulate preferably has a particle size distribution (as determined by Malvern particle size analysis) as follows:

D (v, 0.1)=15-21 μm
D (v, 0.5)=70-120 μm
D (v, 0.9)=190-330 μm

Where the first granulate is to be mixed with further components before tabletting, such further components will typically be one or more of the following: further active agents, e.g. vitamins, in particularly vitamin D, especially vitamin $D_3$; effervescing agents; diluents; sweeteners; flavors; acidulants; and lubricants, e.g. hydrogenated fatty acids, polyethyleneglycol, sodium stearyl fumarate, stearic acid and salts thereof, for example magnesium stearate. When a further active agent is added, this should be at a therapeutically effective dosage. When vitamin D is added, e.g. to produce a product suitable for treatment or prophylaxis of osteoporosis, this preferably is at a calcium to vitamin D ratio of 100 mg Ca: 30 to 150 IU Vitamin D, especially 100:35 to 100 IU, more especially 100:40 to 90 IU. Preferably the second granulate should be such as to be tablettable to produce tablets containing 500 mg Ca and 200 to 250 IU or 400 to 450 IU vitamin $D_3$.

Where vitamin D is used, this may conveniently be vitamin $D_2$ (ergocalciferol) or more preferably vitamin $D_3$ (cholecalciferol). Dose units of the second granulate, e.g. tablets formed therefrom, preferably contain 250 to 1500 mg Ca and 5 to 30 μg vitamin D.

Vitamin $D_3$ is commercially available from Roche in a granular form which consists of vitamin $D_3$ in edible fats finely dispersed in a starch coated matrix of gelatin and sucrose with D,L-α-tocopherol added as an antioxidant. However, other dry powder or granulate forms of vitamin D may also be used.

A chewable tablet containing 500 mg calcium and 5 μg vitamin $D_3$ only contains 2.2 mg of the commercial quality of vitamin $D_3$ from Roche (100 CWS). This constitutes only 0.13% of the total weight of the tablet and one may thus anticipate problems with the homogeneity of vitamin $D_3$ in the tablet. A Malvern particle size analysis of the 100 CWS quality typically gives the following results for the particle size distribution: D(v, 0.1)=180-250 μm, D(v, 0.5)=240-300

μm and D(v, 0.9)=320-400 μm. It has been found desirable to sieve the vitamin $D_3$ on 60 mesh (250 μm) with a Russell vibrating sieve. This procedure will increase the number of vitamin $D_3$ particles per tablet and thus facilitate a more even and uniform distribution. In addition to this the sieving procedure will also eliminate all the coarse particles in the vitamin $D_3$ which also contribute to an inhomogeneous distribution.

Twenty consecutive batches of a chewable tablet containing 500 mg calcium and 5 μg vitamin $D_3$ have been produced which have utilized a sieved (<60 mesh) vitamin $D_3$ with a mean particle size in the region of 203-217 μm. All twenty batches comply with the requirements set in the European Pharmacopeia with respect to the uniformity of content of vitamin $D_3$ in the tablet.

Other active ingredients can be included in the compositions produced according to the invention. Examples include isoflavones, vitamin K, vitamin C, vitamin $B_6$ and oligosaccharides such as inulin and oligofructose. Isoflavones exhibit a weak oestrogenic effect and can thus increase bone density in post-menopausal women. Isoflavones are available under the trade name Novasoy 400 from ADM Nutraceutical, Illinois, USA. Novasoy 400 contains 40% isoflavones and will typically be used in an amount sufficient to provide 25 to 100 mg isoflavone/dosage. Isoflavones may be included in the second granulate; however as Novasoy 400 is a relatively cohesive powder it is preferred that it be included in the first granulate in order to ensure that it is uniformly distributed. Vitamin K (more especially vitamin $K_1$) may improve biochemical markers of bone formation and bone density and low concentrations of vitamin $K_1$ have been associated with low bone mineral density and bone fractures. Vitamin $K_1$ is available from Roche as Dry Vitamin $K_1$, 5% SD, a dry substance containing 5% vitamin $K_1$. Typically vitamin $K_1$ will be used in a quantity sufficient to provide 0.05 to 5 mg vitamin $K_1$/dosage. Vitamin C and vitamin $B_6$ (available from Roche, Takeda and BASF amongst others) function as cofactors in the formation of collagen, the main component of the organic matrix of bone. Vitamin C and vitamin $B_6$ will typically be used in quantities sufficient to provide 60 to 200 mg vitamin C/dosage and 1.6 to 4.8 mg vitamin $B_6$/dosage respectively. Oligosaccharides have been shown to facilitate and increase calcium absorption and may typically be used in quantities sufficient to provide 0.3 to 5 g oligosaccharide/dosage. In general it is desirable that a total of at least 5 g oligosaccharide is administered daily to facilitate calcium uptake and to obtain a pre-biotic effect.

Where an active component is used which forms a minor part of the overall granulate, e.g. vitamin D, it is general preferred to produce a premix of such a component and the first granulate before mixing the premix and the remaining required quantity of the first granulate. This ensures uniform distribution of the minor component in the second granulate.

The second granulate also preferably contains a flavor, e.g. a fruit flavor, in particular a lemon or orange flavor, in order to mask the chalky taste of calcium carbonate. The flavor may, for example, be a lemon or orange oil dispersed in a hydrogenated glucose syrup material or, alternatively, it may be any other stable flavor, e.g. one of the Durarome flavors available from Firmenich.

Extra sweeteners, e.g. artificial sweeteners such as aspartame, acesulfame K, saccharin, sodium saccharin, neohesperidine hydrochloride, taumatin and sodium cyclamate may be used to enhance the sweetness of the granulate.

Acidulants, e.g. anhydrous citric acid, malic acid, or any other organic acid with suitable organoleptic properties may be used in order to complement and enhance the flavour and sweetness of the dosage form.

Such extra components may be mixed in during the fluid granulation step of the process of the invention, but preferably they are mixed in with the first granulate in a separate dry mixing step, optionally after a sieving step to ensure homogeneous mixing.

When the granulate is to be tabletted, it preferably includes a lubricant, e.g. magnesium stearate, stearic acid, hydrogenated fatty acids, sodium stearyl fumarate, PEG 6000 or PEG 8000. Magnesium stearate is generally preferred. Such a lubricant will generally make up 0.3 to 1.5%, particularly 0.35 to 1.0% by weight of the composition to be tabletted. The lubricant is preferably added in a final mixing step and mixed in for a brief time to prevent overmixing and subsequent lack of cohesion in the tabletted product.

Where the granulate is to be tabletted, this can be effected on conventional tablet presses. Preferably the tablet so produced will have a total weight of 500 to 3800 mg, e.g. 500 to 3000 mg, more especially 1000 to 2500 mg, most preferably 1500 to 2000 mg. If desired however, the granulate (either the first granulate or the second granulate) may be used for other administration forms, e.g. powders, capsules, lozenges, coated tablets, etc. In general dose units (e.g. tablets or sachet contents) will contain 100 to 1000 mg Ca, especially 250 to 750 mg Ca, most preferably 450 to 550 mg Ca. The granulate is itself novel and forms a further aspect of the invention. Viewed from this aspect, the invention provides a granulate, preferably a tablettable granulate, comprising a fluid bed granulation granulate product of a physiologically tolerable calcium compound, a water-soluble binder and a water-soluble diluent, said calcium compound having a mean particle size in the range 3 to 40 μm, having a crystalline structure and having a surface area of 0.1 to 1.2 $m^2/g$.

The calcium compound for preparation of the granulate may, for example, be selected from calcium carbonate, calcium lactate, calcium gluconate, calcium citrate, calcium glycerophosphate, calcium phosphate, calcium hydrogen phosphate, calcium glucuronate, calcium aspartate, calcium glucoheptonate and mixtures of two or more thereof.

The water-soluble diluent included in the granulate is preferably a sweetener or mixture of sweeteners, e.g. a polyol or a polysaccharide, more preferably a non-cariogenic sweetener. Examples of suitable diluents include sorbitol, xylitol, mannitol, sucrose, fructose, maltodextrin, inulin and oligofructose.

The water-soluble binder included in the granulate may be selected from known water-soluble pharmaceutical binders, e.g. it may be a soluble cellulose or polysaccharide or a polyvinylpyrrolidone or a mixture thereof. Maltodextrin and inulin may also be used as binders.

Other active ingredients can also be included in the granulate of the invention. Examples include vitamin $B_6$, vitamin K, vitamin C, vitamin D, isoflavones, inulin and oligofructose and mixtures of two or more thereof.

Viewed from a further aspect, the invention provides a physiologically tolerable particulate calcium compound having a mean particle size in the range 3 to 4 μm, having a crystalline structure and having a surface area of 0.1 to 1.2 m$^2$/g produced by the process of the invention.

Viewed from a still further aspect the invention provides an orally administrable calcium composition, preferably in tablet (e.g. compressed tablet) form, comprising a physiologically tolerable particulate calcium compound having a mean particle size in the range 3 to 40 μm, having a crystalline structure and having a surface area of 0.1 to 1.2 m$^2$/g, a water-soluble diluent, and a water soluble binder; e.g. calcium carbonate, sorbitol and PVP, and preferably also a sweetener, a flavour and a lubricant, e.g. aspartame, citrus oil and magnesium stearate. Especially preferably the composition is in the form of a tablet comprising 1250±10% parts by weight calcium carbonate, (e.g. as Scoralite 1A and/or 1B), 390±10% parts by weight sorbitol, and 36.4±10% parts by weight PVP, and preferably each tablet contains 1250±10% mg calcium carbonate.

The present invention makes it possible to reduce the amount of soluble diluent and binder in a chewable calcium tablet while sustaining the desirable chewability by the production of a highly porous granulate by fluid bed granulation using a calcium compound with a relatively high degree of crystallinity and with smooth faces to the crystals. This high degree of porosity, desirably 20 to 30%, results in the final chewable tablet having improved sensoric properties despite having a high calcium content. Such properties include improved dispersion in water and reduced stickiness during mastication.

The porosity of the granulate or tablet may be determined using mercury intrusion porosimetry (e.g. using a Carlo Erba Porosimeter 2000), and by helium adsorption, e.g. using an AccuPyc 1330 pycnometer to measure true density and a Geopyc 1360 envelope measuring apparatus. AccuPyc 1330 and Geopyc 1360 apparatus are available from Micrometrics. Mercury intrusion porosimetry is the more suitable of the two techniques for measuring the porosity of a granulate while both techniques can be used for measuring the porosity of a tablet.

Viewed from a further aspect the invention provides a tablet (e.g. a lozenge, chewable tablet or a effervescent tablet) comprising a compressed granulate according to the invention and containing: calcium carbonate; vitamin D$_3$; a lubricant; citric acid; and an oligosaccharide; and, optionally but preferably, polyvinylpyrrolidone.

The invention will now be described further with reference to the following non-limiting Examples and the accompanying drawings in which FIGS. 1 to 6 are scanning electron micrographs of six different grades of calcium carbonate and FIGS. 7A, 7B, 8A and 8B are scanning electron micrographs of granulates prepared according to the invention at lower (FIGS. 7A and 8A) and higher (FIGS. 7B and 8B) magnification:

EXAMPLE 1

Preparation of First Granulate

A binder solution is prepared containing 27.7% by weight of polyvinylpyrrolidone (Kollidon K30) in purified water. This is temperature-controlled at 20° C. or more preferably 25° C. before spraying.

A batch of 74.5 parts by weight calcium carbonate (Scoralite 1B) and 23.3 parts by weight sorbitol (Neosorb P100T) is blended for two minutes using a high speed mixer (Fielder PMA 25/2 G) set at maximum mixing speed. 3.0 kg of this blend are then placed at 23-26° C. in the mixer chamber of a Glatt GPCG3 fluid bed mixer.

The polyvinylpyrrolidone solution is then sprayed onto the fluidized blend at a rate of 40 g/min until a total of 280 g of liquid has been added. Spraying is effected into air at an inlet temperature of 45° C. and at ambient pressure.

Air at 70° C. is then passed through the sprayed granulate until it is dry (about 0.2% by weight residual moisture content). At this stage, the granulate temperature is about 44° C. The total duration of the spraying and drying stage is about 25 minutes.

At the end of the drying stage the first granulate has the following properties:

mean particle size and distribution D(v, 0.1)=16 μm, D(v, 0.5)=100 μm, and D(v, 0.9) 284 μm Bulk density: 0.73 g/mL Porosity: 20-30%

Flowability (Carrs index %): 13

The mean particle size analysis is performed on a Malvern Mastersizer S long bench apparatus D(v,0.1), D(v,0.5), and D(v,0.9) give the particle sizes for which 10%, 50% and 90% of the particles by volume have sizes below the given values.

EXAMPLE 2

Preparation and Tabletting of Second Granulate 4.4 parts by weight of sieved (<60 mesh) Vitamin D$_3$ from Roche and 32 parts by weight of the first granulate are dry mixed in a twin cone convection blender to form a pre-mix.

The pre-mix, the first granulate, lemon flavour granulate and aspartame are then dry mixed in a conical screw mixer to produce a granulate which is then mixed for 9 minutes. Magnesium stearate is added and mixed for an additional 3 minutes to produce a second granulate comprising:

| | |
|---|---|
| Calcium carbonate | 1250 parts by weight |
| Sorbitol | 390 parts by weight |
| Polyvinylpyrrolidone | 36.4 parts by weight |
| Vitamin D$_3$ 100 000 IU/g (100 CWS from Roche) | 4.4 parts by weight |
| Lemon flavour (in dehydrated glucose syrup) | 50.7 parts by weight |
| Aspartame | 1 parts by weight |
| Magnesium stearate | 6 parts by weight |

This mixture is then tabletted to produce biconvex tablets of 16 mm diameter containing 1250 mg calcium carbonate.

The characteristics of the tablets are as follows:

Breaking strength: The chewable tablet has a normal biconvex shape and a diameter of 16 mm. The tablet initially has a breaking strength of 6 to 7.5 kp which can increase to approximately 8 to 9 kp after 24 hour storage. This breaking strength gives a satisfactory chewability and at the same time resistance towards handling and packaging into tablet bottles.

The initial breaking strength values may however vary between 4.5 to 8.0 kp according to the size of the tablet (12-21 mm).

Friability: A breaking strength of 6 to 7.5 kp for a chewable tablet with a diameter of 16 mm results in friability values of less than 1%. This low value for the friability ensures sufficient firmness with respect to handling and packaging.

Disintegration: A characteristic feature of this chewable tablet formulation is the very fast disintegrating time.

The disintegration time is typically between 3 and 6 min. It is also a characteristic feature of the tablet that it disintegrates into the primary crystals of calcium carbonate which ensures a rapid exposure of calcium carbonate for dissolution.

This is important for the in vivo dissolution of calcium carbonate in the acidic gastric medium in the stomach and the subsequent absorption of calcium in the gastrointestinal tract.

Porosity: The tablet has a characteristic porosity of 25-30%. The porosity is determined by both mercury intrusion porosimetry and helium adsorption as described above. Both techniques gave porosity values in the range 25-30% for the tablet.

Dissolution: The dissolution rate is typically quick with 90% elemental calcium being dissolved within 10 min in 900 ml of 0.1 N HCl at 37° C. (Ph. Eur., rotating paddle at 50 RPM).

EXAMPLE 3

Lozenge to be Sucked

Using a process analogous to that of Examples 1 and 2 lozenges are prepared with the following composition:

| | |
|---|---|
| Calcium granulate: | |
| Calcium carbonate (Scoralite 1B): | 1250 mg |
| Xylitol (CM50): | 390 mg |
| Polyvinylpyrrolidone (Kollidon K 30): | 36.40 mg |
| Vitamin $D_3$ 100 000 IU/g (100 CWS from Roche): | 4.4 mg |
| Lemon flavor: | 50.7 mg |
| Anhydrous citric acid: | 8.0 mg |
| Aspartame: | 1.0 mg |
| Magnesium stearate: | 6.0 mg |
| Sum tablet weight: | 1747 mg |

EXAMPLE 4

Sachet Product to be Dispersed in a Glass of Water

Using a process analogous to that of Examples 1 and 2 but with sorbitol replaced by anhydrous citric acid, sachets are prepared with the following granulate contents:

| | |
|---|---|
| Calcium granulate: | |
| Calcium carbonate (Scoralite 1A): | 1250 mg |
| Citric acid, anhydrous (powder quality): | 2150 mg |
| Polyvinylpyrrolidone (Kollidon VA 64 or 90F): | 36.60 mg |
| Vitamin $D_3$ 100 000 IU/g (100 CWS from Roche): | 4.4 mg |
| Lemon flavor: | 300 mg |
| Aspartame: | 15.0 mg |
| Acesulfam K: | 14.0 mg |
| Sum sachet contents weight: | 3770 mg |

EXAMPLE 5

Granulate to be Dispensed from a Granulate Dispensing Unit

This product may be used as a food additive or as a functional food where the consumer takes a dosage equivalent to 500-1000 mg of elemental calcium and uses this as a supplement in daily food products, such as for example breakfast cereals and fruit juices. The granulate is produced by a process analogous to that of Examples 1 and 2 with the following composition:

| | |
|---|---|
| Calcium granulate: | |
| Calcium carbonate (Scoralite 1A + 1B): | 1250 mg |
| Xylitol (CM 50): | 390 mg |
| Polyvinylpyrrolidone (Kollidon VA 64): | 36 mg |
| Granulate weight per 500 mg $Ca^{2+}$: | 1676 mg |

In this Example, polyvinylpyrrolidone may be replaced by inulin (e.g. Raftiline ST), 36.60 mg. Additional inulin or oligofructose may be added to bring the total oligosaccharide content to 1 to 5 g per dosage.

EXAMPLE 6

Effervescent Tablet to be Dispersed in a Glass of Water

Using a process analogous to that of Examples 1 and 2, effervescent tablets are prepared with the following composition:

| | |
|---|---|
| Calcium granulate: | |
| Calcium carbonate (Scoralite 1A + 1B): | 1250 mg |
| Citric acid, anhydrous (powder quality) | 2150 mg |
| Polyvinylpyrrolidone (Kollidon VA 64 or 90F): | 36.60 mg |
| Vitamin $D_3$ 100 000 IU/g (100 CWS from Roche): | 4.4 mg |
| Lemon flavor: | 300 mg |
| Aspartame: | 15.0 mg |
| Acesulfam K: | 15.0 mg |
| Sodium stearate fumarate: | 19.0 mg |
| Sum tablet weight: | 3790 mg |

In this Example, aspartame and acesulfam K may be partially or totally replaced by inulin or oligofructose with these providing 1 to 4 oligosaccharide per tablet.

EXAMPLE 7

Calcium Carbonate Grades

Samples of Scoralite 1B, Scoralite 1B, Super Purity $CaCO_3$, Medicinal Heavy $CaCO_3$, Pharmacarb LL and Merck 2064 were investigated using a scanning electron microscope (SEM). SEM pictures of these grades of calcium carbonate are presented in FIGS. 1 to 6 respectively of the accompanying drawings.

Granulates made analogously to Example 1 using Scoralite 1B and Super Purity $CaCO_3$ were also investigated by SEM and SEM pictures of these granulates at lower (A) and higher (B) magnifications are presented in FIGS. 7 and 8 of the accompanying drawings. The pictures of the two granulates clearly show their high degree of porosity, a property which is important for the fast disintegration/dissolution of tablets made therefrom. Moreover, this high degree of porosity is important for the sensory properties such as chewability and avoidance of sticking to the teeth during mastication.

EXAMPLES 8 TO 12

Analogously to Examples 1 and 2, chewable tablets and lozenges are prepared with the compositions set out in Table 1 below. The difference between a chewable tablet and a lozenge is simply in crushing strength or hardness, the lozenge being more forceably compressed so that it can be sucked and will last longer in the mouth.

The concentration of the binder in the aqueous granulation liquid and the granulation spray rate are adjusted in Examples 9 to 12 as follows:

Example 9: 20% maltodextrin solution, spray rate 31 g/min.
Example 10: 15% inulin solution, spray rate 28 g/min.
Example 11: 15% inulin solution, spray rate 31 g/min.
Example 12: 28% PVP solution, spray rate 31 g/min.

|  | Example Number | | | | |
|---|---|---|---|---|---|
|  | 8 | 9 | 10 | 11 | 12 |
| Ingredients in calcium granulate | | | | | |
| CaCO$_3$[1] | 1250 mg | 1250 mg | 1250 mg | 1250 mg | 1250 mg |
| Isoflavone extract[2] | — | — | — | — | 62.5 mg |
| Xylitol[3] | 390 mg | — | — | — | 389 mg |
| Sucrose[4] | — | 391 mg | — | — | — |
| Inulin[5] | — | — | 390 mg | — | — |
| Isomalt[6] | — | — | — | 390 mg | — |
| Polyvinyl-pyrrolidone VA64 | 36.40 mg | — | — | — | 45.50 mg |
| Inulin[5] | — | — | 24.00 mg | 24.00 mg | — |
| Maltodextrin[7] | — | 31.00 mg | — | — | — |
| Remaining Ingredients | | | | | |
| Vitamin D$_3$[8] | 4.4 mg | 4.4 mg | 4.4 mg | 4.4 mg | 4.4 mg |
| Lemon Flavour | 53.2 mg | 52.6 mg | 52.6 mg | 52.6 mg | 52.6 mg |
| Anhydrous Citric Acid | 8.0 mg | — | — | — | — |
| Malic Acid | — | 8.0 mg | 8.0 mg | 8.0 mg | 8.0 mg |
| Aspartame | — | — | 1.0 mg | 1.0 mg | — |
| Magnesium Stearate | 8.0 mg | 8.0 mg | 8.0 mg | 8.0 mg | 8.0 mg |
| Tablet Weight | 1750 mg | 1745 mg | 1738 mg | 1738 mg | 1820 mg |

[1]Scoralite 1A + 1B
[2]Novasoy 400
[3]CM 50
[4]Tate & Lyle
[5]Raftiline ST
[6]Isomalt PF
[7]Lycatab DSH
[8]100 CWS In Examples 10 and 11, additional oligosaccharide (e.g. inulin or oligofructose) may be added to bring the oligosaccharide content to 1 to 5 g per dosage.

EXAMPLE 13

Calcium Carbonate Characteristics

Different samples (lots) of Scoralite 1B and Scoralite 1A+1B were investigated for particle size (using Malvern Particle size analysis performed on a Malvern Mastersizer S long bench apparatus and a Malvern Mastersizer 2000), specific surface area (BET analysis by nitrogen adsorption performed on a Sartorius micro balance) and apparent bulk density (using apparent bulk density before settling (poured density) according to Ph. Eur., 3rd Edition, 1977). The values determined were as follows:

|  | Scoralite Sample | | | | | |
|---|---|---|---|---|---|---|
|  | 1B | 1B | 1B | 1A + 1B | 1A + 1B | 1A + 1B |
| Apparent bulk density (g/mL) | 1.09 | 1.04 | 1.02 | 0.95 | 0.99 | 0.89 |
| D(v, 0.5) μm | 15.1 | 14.7 | 15.9 | 13.3 | 13.7 | 11.8 |
| D(v, 0.1) μm | 8.8 | 8.7 | 8.1 | 6.3 | 6.5 | 3.9 |
| D(v, 0.9) μm | 24.3 | 23.4 | 27.8 | 23.5 | 24.2 | 23.0 |
| Specific surface area (m$^2$/g) | 0.5 | 0.5 | 0.5 | 0.4 | 0.5 | 0.7 |

The invention claimed is:

1. A process for the preparation of an orally administrable calcium composition, said process comprising the steps of:
   (i) obtaining a physiologically tolerable particulate calcium compound having a mean particle size in the range 3 to 40 μm, having a crystalline structure and having a surface area of 0.1 to 1.2 m$^2$/g;
   (ii) mixing said calcium compound with a water-soluble diluent and an aqueous solution of a water soluble binder in a fluid bed granulation apparatus and drying the resulting mixture to produce a first granulate;
   (iii) mixing said first granulate with one or more further components to produce a second granulate; and
   (iv) compressing said first or second granulate to form tablets having a porosity of from 25-30%.

2. A process as claimed in claim 1 wherein said calcium compound is selected from the group consisting of calcium carbonate, calcium lactate, calcium gluconate, calcium citrate, calcium glycerophosphate, calcium phosphate, calcium hydrogen phosphate, calcium glucuronate, calcium aspartate, calcium glucoheptonate and mixtures of two or more thereof.

3. A process as claimed in claim 1 wherein said calcium compound is calcium carbonate.

4. A process as claimed in claim 1 wherein said calcium compound makes up 68 to 80% wt. of said first granulate.

5. A process as claimed in claim 1 wherein said calcium compound makes up 60 to 95% wt. of said second granulate.

6. A process as claimed in claim 1 wherein in step (i) the same material is used as said diluent and as said binder.

7. A process as claimed in claim 1 wherein said water-soluble diluent comprises at least one sweetener.

8. A process as claimed in claim 7 wherein said sweetener is selected from the group consisting of sorbitol, xylitol, isomalt, mannitol, sucrose, fructose, maltodextrin, inulin and oligofructose.

9. A process as claimed in claim 1 wherein said water-soluble diluent makes up 70 to 96% wt. of the total weight of said water-soluble diluent and said water-soluble binder in said first granulate.

10. A process as claimed in claim 1 wherein said water-soluble binder is selected from the group consisting of celluloses, polysaccharides, maltodextrin, inulin and polyvinylpyrrolidone.

11. A process as claimed in claim 1 wherein said water-soluble binder is a polyvinylpyrrolidone.

12. A process as claimed in claim 1 wherein said first granulate has a particle size distribution of 0 (V, 0.1)=15-21 µm, D (V, 0.5)=70-120 µm and D (V, 0.9)=190-330 µm.

13. A process as claimed in claim 1 wherein a said further component is mixed with said first granulate, said further component being selected from the group consisting of vitamin $B_6$, vitamin K, vitamin C, vitamin D, isoflavones, inulin, and oligofructose and mixtures of two or more thereof.

14. A process as claimed in claim 1 wherein in step (ii) said calcium compound is also mixed with isoflavones.

15. A tablet comprising a compressed granulate comprising a fluid bed granulation granulate product of a physiologically tolerable calcium compound, a water-soluble binder and a water-soluble diluent, said calcium compound having a mean particle size in the range 3 to 40 µm, having a crystalline structure and having a surface area of 0.1 to 1.2 $m^2/g$, and containing: calcium carbonate; vitamin $D_3$; a lubricant; citric acid; and an oligosaccharide, said tablet having a porosity of from 25-30% and having a dissolution rate where 90% of the elemental calcium is dissolved within 10 minutes.

16. A process as claimed in claim 1, wherein the tablets have a dissolution rate where 90% of the elemental calcium is dissolved within 10 minutes.

* * * * *